United States Patent
Lin et al.

(10) Patent No.: US 11,497,506 B2
(45) Date of Patent: Nov. 15, 2022

(54) CLAMPING INSTRUMENT AND CLAMPING ASSEMBLY

(71) Applicant: SHANGHAI HUIHE HEALTHCARE TECHNOLOGY CO., LTD., Shanghai (CN)

(72) Inventors: Lin Lin, Shanghai (CN); Bao Wang, Shanghai (CN)

( * ) Notice: Subject to any disclaimer, the term of this patent is extended or adjusted under 35 U.S.C. 154(b) by 285 days.

(21) Appl. No.: 16/851,087

(22) Filed: Apr. 16, 2020

(65) Prior Publication Data
US 2021/0059680 A1    Mar. 4, 2021

Related U.S. Application Data

(63) Continuation of application No. PCT/CN2020/080406, filed on Mar. 20, 2020.

(30) Foreign Application Priority Data

Aug. 28, 2019   (CN) .......................... 201910804053.1

(51) Int. Cl.
*A61B 17/122*     (2006.01)
*A61B 17/128*     (2006.01)
(Continued)

(52) U.S. Cl.
CPC ........ *A61B 17/122* (2013.01); *A61B 17/1285* (2013.01); *A61B 2017/00243* (2013.01); *F16B 2/10* (2013.01)

(58) Field of Classification Search
CPC . A61B 17/122; A61B 17/128; A61B 17/1285; A61B 2017/2931; A61B 2017/2932
See application file for complete search history.

(56) References Cited

U.S. PATENT DOCUMENTS

| | | | | |
|---|---|---|---|---|
| 7,226,467 B2 * | 6/2007 | Lucatero | ............ | A61B 18/1492 606/213 |
| 7,604,646 B2 * | 10/2009 | Goldfarb | ................. | A61F 2/246 606/151 |
| 7,635,329 B2 * | 12/2009 | Goldfarb | ................ | A61B 17/08 600/37 |

(Continued)

FOREIGN PATENT DOCUMENTS

| CN | 206414334 U | 8/2017 |
|---|---|---|
| CN | 206714786 U | 12/2017 |

(Continued)

OTHER PUBLICATIONS

Interbational search report of PCT/CN2020/080406.

*Primary Examiner* — Ryan J. Severson

(57) ABSTRACT

The invention provides a clamping instrument and a clamping assembly, which mainly comprises a positioning base, a moving base, at least two clamping arms connected with the moving base, at least two linkage arms respectively connected with each of the clamping arms and the positioning base, and an actuating rod respectively penetrating through the positioning base and the moving base, wherein the positioning base is rotated circumferentially and fixed axially relative to the actuating rod, and the moving base is rotated circumferentially and moves axially relative to the actuating rod; when the movable rod is rotated circumferentially, a distance between the moving base and the positioning base can be changed, and then each of the clamping arms is linked to be rotated around the moving base to be in an unfolded position or a clamped position so as to clamp a preset site of a human tissue. Thus, the rotating amplitude of the clamping arms can be finely adjusted to provide a clamping force with high precision in the present invention.

14 Claims, 14 Drawing Sheets

(51) Int. Cl.
 *A61B 17/00* (2006.01)
 *F16B 2/10* (2006.01)

(56) References Cited

U.S. PATENT DOCUMENTS

| | | | | |
|---|---|---|---|---|
| 7,811,296 | B2* | 10/2010 | Goldfarb | A61B 17/1285 606/151 |
| 8,052,592 | B2* | 11/2011 | Goldfarb | A61B 17/08 600/37 |
| 8,343,174 | B2* | 1/2013 | Goldfarb | A61B 17/00234 606/151 |
| 8,858,588 | B2* | 10/2014 | Sigmon, Jr. | A61B 17/10 606/205 |
| 8,945,177 | B2* | 2/2015 | Dell | A61B 17/10 606/213 |
| 10,667,815 | B2* | 6/2020 | Krone | A61B 17/08 |
| 11,065,119 | B2* | 7/2021 | Abunassar | A61B 17/08 |
| 2002/0058961 | A1* | 5/2002 | Aguilar | A61M 29/02 606/198 |
| 2006/0020275 | A1* | 1/2006 | Goldfarb | A61F 2/246 606/151 |
| 2009/0163934 | A1* | 6/2009 | Raschdorf, Jr. | A61B 17/00234 606/139 |
| 2009/0326567 | A1* | 12/2009 | Goldfarb | A61B 17/00234 606/157 |
| 2010/0022823 | A1* | 1/2010 | Goldfarb | A61B 17/0401 600/37 |
| 2012/0089176 | A1* | 4/2012 | Sigmon, Jr. | A61B 17/08 606/205 |
| 2017/0020521 | A1* | 1/2017 | Krone | A61B 17/08 |
| 2018/0325671 | A1 | 11/2018 | Abunassar et al. | |
| 2021/0059680 | A1* | 3/2021 | Lin | A61B 17/122 |

FOREIGN PATENT DOCUMENTS

| | | |
|---|---|---|
| CN | 107920813 A | 4/2018 |
| CN | 208876682 U | 5/2019 |
| CN | 209220375 U | 8/2019 |
| CN | 110403670 A | 11/2019 |
| WO | 2005112792 A2 | 12/2005 |

* cited by examiner

CLAMPING INSTRUMENT AND CLAMPING ASSEMBLY

This application claims priority to the prior application No. CN201910804053.1, filed on Aug. 28, 2019, entitled "Clamping Instrument and Clamping Assembly", the contents of which are incorporated herein by reference.

TECHNICAL FIELD

The embodiment of the invention relates to the field of medical instruments, in particular to a clamping instrument and a clamping assembly for a heart valve annulus.

BACKGROUND

The tricuspid valve is located in the right atrioventricular ostium, and the common pathogenesis is tricuspid insufficiency, i.e. systolic blood flows from the right ventricle back into the right atrium, resulting in the enlargement of the right atrium, with increased pressure and venous blood reflux disturbance. A right heart failure is prone to occur due to increased right ventricular load and compensatory hypertrophy.

Tricuspid regurgitation is usually caused by pulmonary hypertension, right ventricular enlargement and dilatation of tricuspid valve annulus. The causes of tricuspid regurgitation (left heart failure, pulmonary hypertension, etc.) are common in clinic. After the tricuspid regurgitation, symptoms of right heart failure such as fatigue, ascites, edema, pain in the liver area, dyspepsia, anorexia, etc. are aggravated. Mild tricuspid regurgitation does not have obvious clinical symptoms, but a surgical treatment is required for severe regurgitation.

Traditional treatments include drug therapy, and surgical procedures with corresponding surgical indications. Among them, surgical methods also include valve replacement and valve repair. In the surgical method, the typical thoracotomy and open heart surgery are too invasive, and it is required to establish a extracorporeal circulation, and the complication rate and the infection risk are high. Many patients cannot tolerate significant surgical risks and only wait helplessly for death.

At present, a plurality of products has been clinically applied for treating tricuspid regurgitation by minimally invasive catheterization. However, the products are all in an experimental stage, without realizing mature applications, and with limitations for respective technologies.

Therefore, how to overcome various limitations in the prior art is the technical problem to be solved by the present application.

SUMMARY

In view of the above problems, the main object of the present application is to provide a clamping instrument and a clamping assembly, which can finely adjust the rotation amplitude of a clamping arm, provide an accurate clamping force, and is not easy to hurt human tissues.

Another object of the present application is to provide a clamping instrument and a clamping assembly, which are simple in structure and convenient to operate, can also be suitable for clamping human tissues of different thicknesses, and have a wide application range.

To achieve the above objects and other related objects, an embodiment of the present application provides a clamping instrument for clamping a preset site of a human tissue, comprising: a positioning base having a first penetrating channel; a moving base having a second penetrating channel; at least two clamping arms, wherein one end of each of the clamping arms is respectively connected with the moving base to enable each of the clamping arms to rotate around the moving base to be in an unfolded position or a clamped position; at least two linkage arms, wherein two ends of each of the linkage arms are respectively connected with the positioning base and each of the clamping arms to enable each of the clamping arms to indirectly connect with the positioning base; and an actuating rod, wherein the actuating rod penetrates through the first penetrating channel and the second penetrating channel respectively to enable the positioning base and the moving base to be coaxially assembled on the actuating rod, the positioning base is rotatable circumferentially around the actuating rod and is axially fixed relative to the actuating rod, and the moving base is rotatable circumferentially around the actuating rod and is axially movable relative to the actuating rod; wherein, when the actuating rod is rotated circumferentially, a distance between the moving base and the positioning base can be changed, and then each of the clamping arms is consequentially linked to be rotated around the moving base; wherein, when in the unfolded position relative to the moving base, each of the clamping arms can be respectively positioned on the preset site of the human tissue; and when each of the clamping arms is in the clamped position relative to the moving base, the preset site of the human tissue can be clamped by the coordination of each of the clamping arms.

Optionally, in an embodiment of the application, when the actuating rod is rotated circumferentially in a first direction, the distance between the moving base and the positioning base is gradually reduced, so that each of the clamping arms is rotated around the moving base to be gradually rotated from the unfolded position to the clamped position; when the actuating rod is rotated circumferentially in a second direction opposite to the first direction, the distance between the moving base and the positioning base is gradually increased, so that each of the clamping arms is rotated around the moving base to be gradually rotated from the clamped position to the unfolded position.

Alternatively, in an embodiment of the present application, the moving base is disposed at a position closer to a distal end of the actuating rod than the positioning base.

Optionally, in an embodiment of the application, a first adjusting unit is further provided on the actuating rod at a position where the moving base is correspondingly provided, and the moving base is provided with a second adjusting unit, wherein the first adjusting unit and the second adjusting unit are structurally adapted to enable the moving base to circumferentially rotate and axially move relative to the actuating rod.

Alternatively, in an embodiment of the present application, the first adjusting unit is an external thread formed on the actuating rod, and the second adjusting unit is an internal thread formed in the second penetrating channel of the moving base.

Optionally, in an embodiment of the present application, the clamping instrument further comprises a limiting structure for defining a maximum range of movement for axial movement of the moving base relative to the actuating rod.

Optionally, in an embodiment of the present application, each of the clamping arms respectively further comprises a proximal end of the clamping arm connected to the moving base, and the limiting structure is provided at the proximal end of each of the clamping arms.

Optionally, in an embodiment of the present application, the clamping instrument further comprises a positioning structure disposed between the actuating rod and the positioning base for limiting axial movement of the actuating rod relative to the positioning base when the actuating rod is rotated circumferentially.

According to another embodiment of the application, the clamping instrument is provided for clamping a preset site of a human tissue, and particularly comprises: a positioning base having a first penetrating channel; a moving base having a second penetrating channel; at least two clamping arms, wherein one end of each of the clamping arms is respectively connected with the positioning base to enable each of the clamping arms to rotate around the positioning base to be in an unfolded position or a clamped position; at least two linkage arms, wherein two ends of each of the linkage arms are respectively connected with the moving base and each of the clamping arms to enable each of the clamping arms to indirectly connect with the moving base; and an actuating rod, wherein the actuating rod penetrates through the first penetrating channel and the second penetrating channel respectively to enable the positioning base and the moving base to be coaxially assembled on the actuating rod, the positioning base is rotatable circumferentially around the actuating rod and is axially fixed relative to the actuating rod, and the moving base is rotatable circumferentially around the actuating rod and is axially movable relative to the actuating rod; wherein, when the actuating rod is rotated circumferentially, a distance between the moving base and the positioning base can be changed, and then each of the clamping arms is consequentially linked to be rotated around the moving base; wherein, when in the unfolded position relative to the moving base, each of the clamping arms can be respectively positioned on the preset site of the human tissue; and when each of the clamping arms is in the clamped position relative to the moving base, the preset site of the human tissue can be clamped by the coordination of each of the clamping arms.

Alternatively, in an embodiment of the present application, the positioning base is disposed at a position closer to the distal end of the actuating rod than the moving base.

Optionally, in an embodiment of the application, the clamping instrument can also be externally connected with a delivery device, and the delivery device is provided with a delivery member and a driving member, wherein the delivery member is connected to the moving base of the clamping instrument for limiting the circumferential rotation of the moving base; and the drive member is connected to the actuating rod of the clamping instrument for driving the actuating rod to be rotated circumferentially.

Optionally, in the embodiment of the application, the delivery member and the driving member are respectively connected to the positioning base and the actuating rod at the proximal end of the actuating rod, or the delivery member and the driving member are respectively connected to the positioning base and the actuating rod at the distal end of the actuating rod, or the delivery member and the driving member are respectively connected to the positioning base and the actuating rod at two ends of the actuating rod.

The invention also provides a clamping assembly used for clamping a preset site of a human tissue, comprising: an auxiliary support used for providing auxiliary supporting inside the human tissue so as to enable the preset site of the human tissue to be in a convex state; and a clamping instrument described in each embodiment used for clamping the preset site in the convex state and the auxiliary support.

Optionally, in an embodiment of the application, the preset site comprises a first side and a second side opposite to each other, wherein the auxiliary support abuts against the preset site at the first side of the preset site, and the clamping instrument clamps the preset site and the auxiliary support at the second side of the preset site, so that the preset site is clamped between the auxiliary support and the clamping instrument.

It can be seen from the above technical solution that the actuating rod is rotated circumferentially relative to the positioning base and the moving base, so as to change the distance between the positioning base and the moving base coaxially assembled on the actuating rod, thereby controlling the clamping arm to be rotated relative to the moving base. Thereby, the rotation amplitude of the clamping arm can be precisely controlled, thus providing the clamping force with high precision, and the clamping device can be applied to clamp human tissues with different thickness.

Furthermore, the auxiliary support is matched with the clamping instrument to clamp the preset site of the human tissue therebetween, so that the human tissue can be prevented from being torn to improve use safety.

BRIEF DESCRIPTION OF THE DRAWINGS

In order to more clearly illustrate embodiments of the present application or technical solutions in the prior art, the drawings used in the embodiments or the description of the prior art will be briefly introduced below. Obviously, the drawings in the following description are just some of the embodiments described in the embodiments of the present application. For those of ordinary skill in the art, other drawings can also be obtained according to these drawings.

Figure 1A:
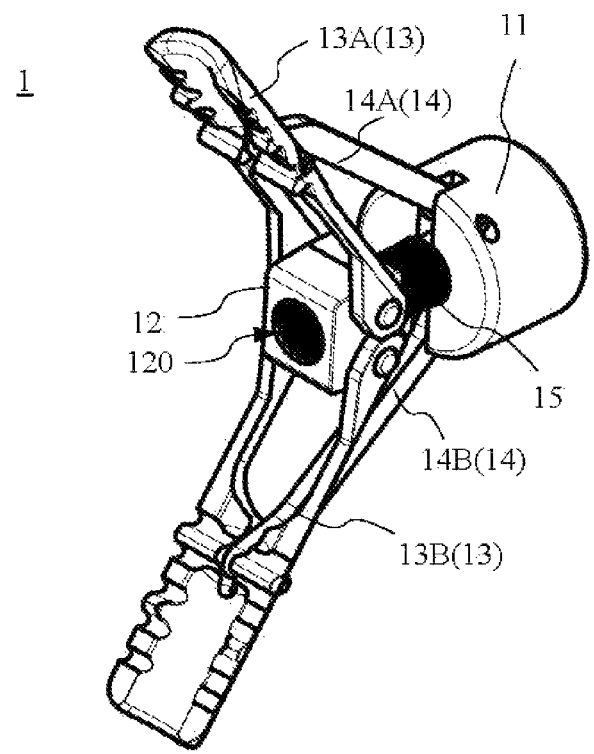
FIGS. 1A and 1B are perspective views showing a clamping instrument in an unfolded state and a clamped state according to a first embodiment of the present application.

REFERENCE NUMERALS 1, a clamping instrument; 11, a positioning base; 110, a first penetrating channel; 12, a moving base; 120, a second penetrating channel; 121, a second adjusting unit; 13, 13A, 13B, a clamping arm; 14, 14A, 14B, a linkage arm; 15, an actuating rod; 151, a first adjusting unit; 16, a limiting structure; 16A, 16B, a spacing unit; 161A, a first unfolded spacing surface; 162A, a first clamping spacing surface; 161B, a second unfolded spacing surface; 162B, a second clamping spacing surface; 17, a positioning structure; 17A, a snap spring; 17B, an anti-loosening gasket; 2, a clamping assembly; 3, an auxiliary support; 4, a delivery device; 41, a delivery member; 42, a driving member; 5, a human tissue; 51, a preset site; 511, a first side; 512, a second side.

DETAILED DESCRIPTION OF THE INVENTION

In order to enable those skilled in the art to better understand the technical solutions in the embodiments of the present application, the technical solutions in the embodiments of the present application will be clearly and completely described below with reference to the accompanying drawings in the embodiments of the present application. Obviously, the described embodiments are only a part of the embodiments of the present application, but not all the embodiments. Based on the embodiments of the present application, all other embodiments obtained by one of ordinary skill in the art should be within the scope of the embodiments of the present application.

As used herein, the term "distal" refers to an end of the clamping instrument (actuating rod) far away from the operator, and the term "proximal" refers to an end of the clamping instrument (actuating rod) near to the operator.

The application mainly provides a clamping instrument and a clamping assembly, which can be used for clamping a preset site 51 (see the figures) of a human tissue 5. In the embodiment, for example, the human tissue 5 is a heart valve annulus. In particular, the clamping device 1 provided by the application belongs to the design of a product for treating tricuspid regurgitation by catheter intervention. Similar to the Kay'S surgical method, two ends of the posterior valve of the tricuspid valve are sewn together in the design, so that the tricuspid valve is bivalved, shortening the whole circumference of the valve ring, and achieving the aim of reducing the regurgitation of the tricuspid valve.

Referring now to FIGS. 1A, 1B, 2A, 2B and 3, there is shown a clamping instrument 1 of a first embodiment of the present application. As shown in the drawings, the clamping instrument 1 of the present application mainly comprises a positioning base 11, a moving base 12, a plurality of clamping arms 13, a plurality of linkage arms 14, and an actuating rod 15.

A first penetrating channel 110 is formed in the positioning base 11, and a second penetrating channel 120 is formed in the moving base 12.

One end of each of the clamping arms 13 is respectively connected to the moving base 12 so as to provide that each of the clamping arms 13 is rotated around the moving base 12 to be in an unfolded position or a clamped position. In the present embodiment, the number of the arrangement of the clamping arms 13 is at least two, which will be described hereinafter with reference to the two clamping arms 13A and 13B shown in the drawings of the present application, but is not limited thereto. The number of the arrangement of the clamping arms 13 can be increased to three or more as required for practical use, as described earlier.

Two ends of each of the linkage arms 14 are respectively connected with the positioning base 11 and each of the clamping arms 13, so that each of the clamping arms 13 is indirectly connected with the positioning base 11. In the embodiment, the number of linkage arms 14 (i.e., linkage arms 14A and 14B as shown) may correspond to the number of clamping arms 13 to provide indirect connection of the clamping arms 13A, 13B to the positioning base 11 via the linkage arms 14A, 14B, respectively, thereby a linkage effect is generated by the clamping arms 13A, 13B as the distance between the positioning base 11 and the moving base 12 is changed (as will be described in detail later). But it is not limited with this, in other embodiments, the number of linkage arms 14 provided is more than the number of clamping arms 13, for example, a plurality of linkage arms 14 may be provided for two clamping arms 13.

The actuating rod 15 penetrates through the first penetrating channel 110 and the second penetrating channel 120 respectively, so that the positioning base 11 and the moving base 12 are coaxially assembled on the actuating rod 15. In the embodiment, the positioning base 11 can be rotated circumferentially but be fixed axially relative to the actuating rod 15, and the moving base 12 can be rotated circumferentially relative to the actuating rod 15 and also can move axially relative to the actuating rod 15.

Figure 1B:
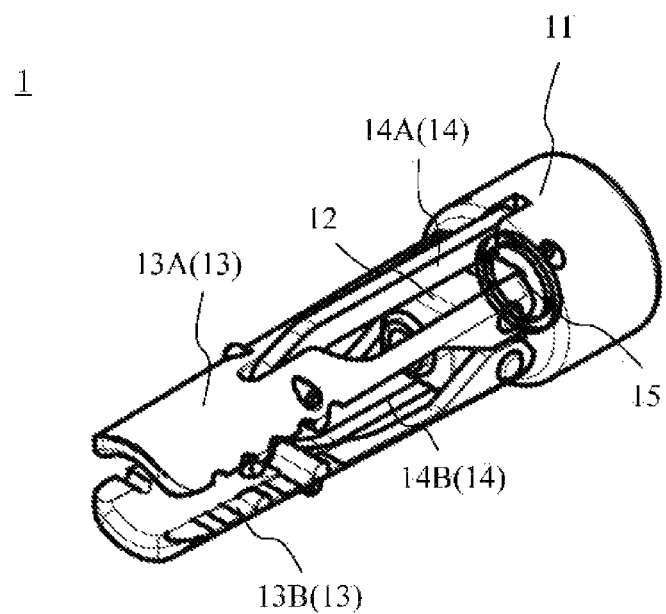
Figure 2A:
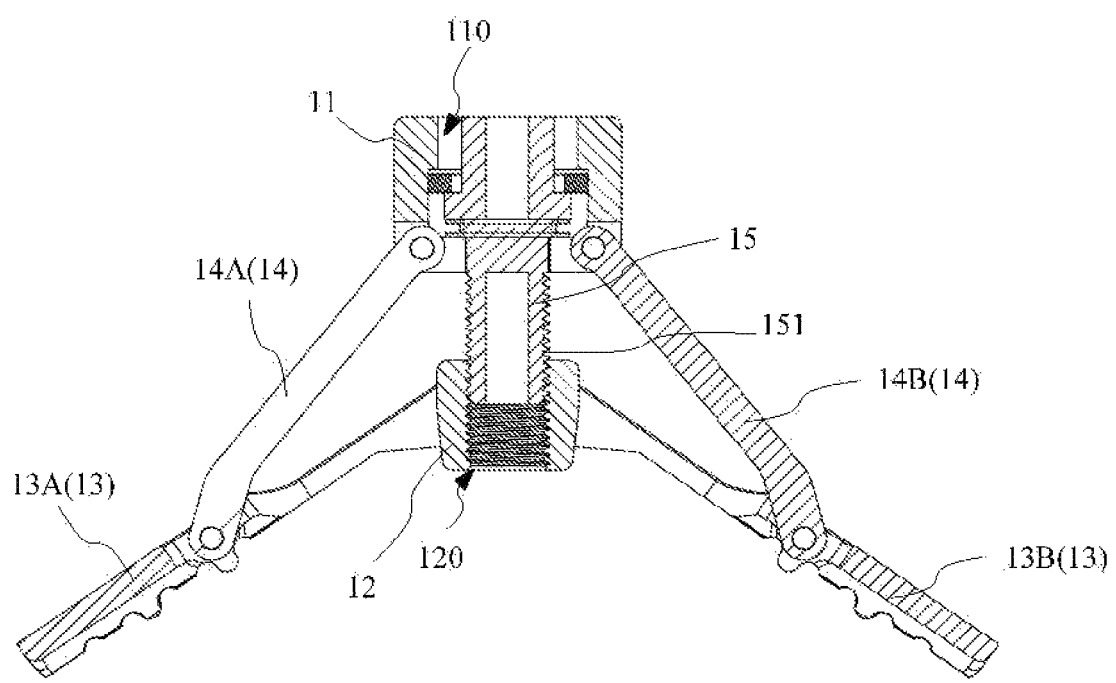
FIGS. 2A and 2B are side cross-sectional views of FIGS. 1A and 1B, respectively.
Figure 2B:
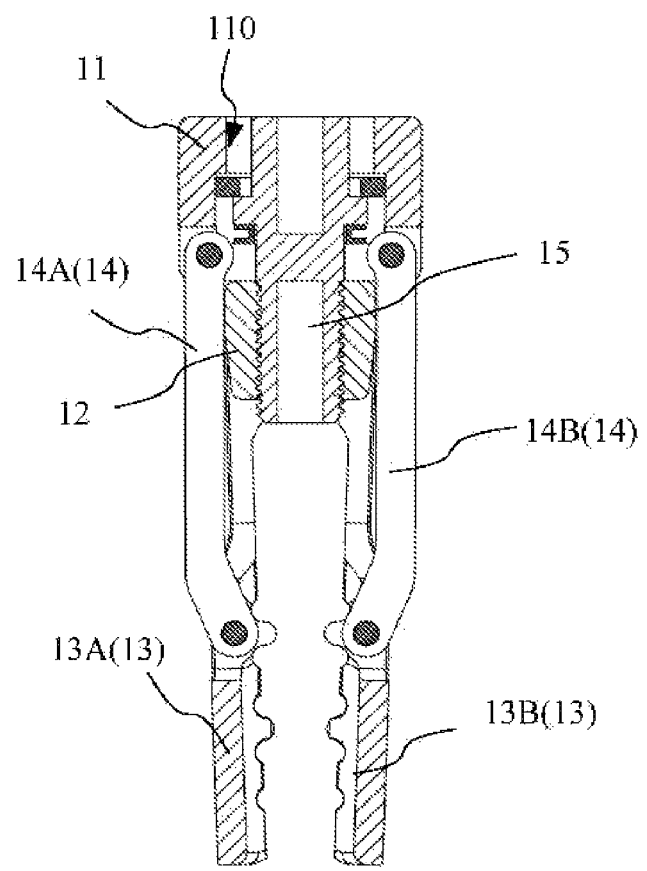
Figure 6A:
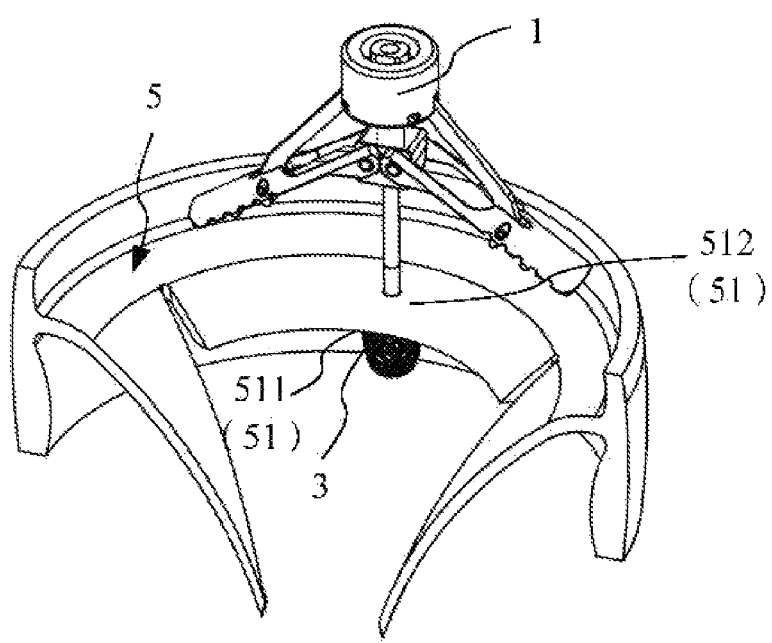
FIGS. 6A and 6B are schematic views showing an embodiment for applying the clamping assembly of the present application.
Figure 6B:
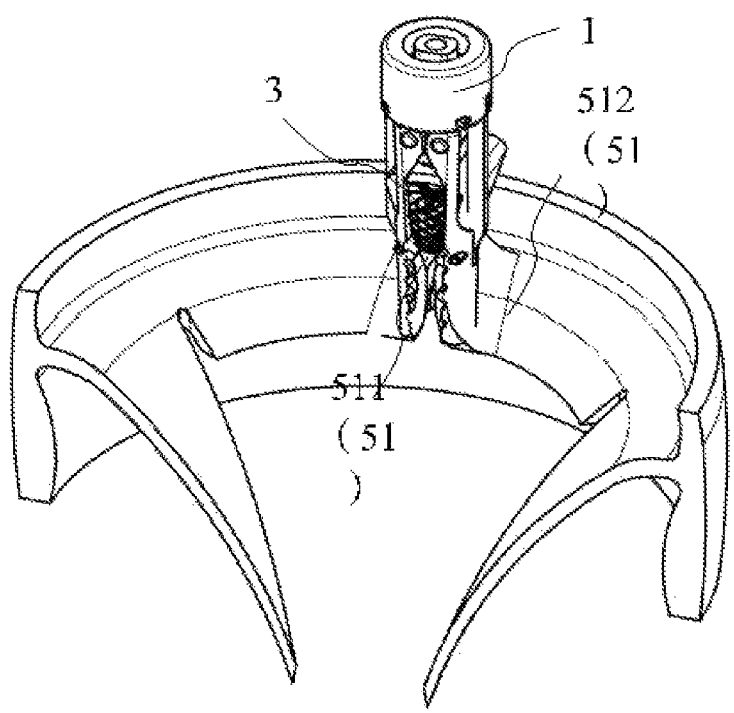

In practice, the distance between the moving base 12 and the positioning base 11 coaxially mounted on the actuating rod 15 can be changed by rotating the actuating rod 15 in the circumferential direction, and then the clamping arms 13A and 13b are linked to be rotated around the moving base 12 to be in an unfolded position (shown in FIGS. 1A and 2A) or a clamped position (shown in FIGS. 1B and 2B). When the clamping arms 13A and 13B are at respective unfolded positions relative to the moving base 12 respectively, the clamping arms 13A and 13B can be respectively positioned on the preset site 51 of the human tissue 5; when the clamping arms 13A, 13B are at their respective clamped positions relative to the moving base 12, the preset site 51 of the human tissue 2 can be clamped therebetween by the coordination between the clamping arm 13A and the clamping arm 13B (as shown in FIGS. 6A and 6B).

In this embodiment, when the actuating rod 15 is rotated circumferentially in the first direction (e.g., clockwise direction), the positioning base 11 and the moving base 12 are simultaneously rotated circumferentially relative to the actuating rod 15, so that when the actuating rod 15 is rotated in the circumferential direction, the positioning base 11 and the moving base 12 are always kept fixed in the circumferential direction; in this state, the positioning base 11 is axially fixed relative to the actuating rod 15, while the moving base 12 is moved axially upward with respect to the actuating rod 15 (i.e. in a direction close to the positioning base 11), so that the distance between the moving base 12 and the positioning base 11 coaxially assembled on the actuating rod 15 is gradually reduced; and in this state, the clamping arms 13A and 13B are gradually rotated around the moving base 12 from the unfolded position shown in FIGS. 1A and 2A to the clamped position shown in FIGS. 1B and 2B. On the contrary, when the actuating rod 15 is rotated circumferentially in a second direction opposite to the first direction (e.g., counter-clockwise direction), the positioning base 11 is fixed axially relative to the actuating rod 15, and the moving base 12 is moved axially downward relative to the actuating rod 15 (i.e., in a direction away from the positioning base 11), so that the distance between the moving base 12 coaxially assembled on the actuating rod 15 and the positioning base 11 is gradually increased. In this state, the clamping arms 13A and 13B are gradually rotated around the moving base 12 from the clamped position shown in FIGS. 1B and 2B to the unfolded position shown in FIGS. 1A and 2A.

In an embodiment, the moving base 12 is disposed at a position closer to the distal end of the actuating rod 15 than the positioning base 11, i.e. in the illustration shown in FIGS. 2A and 2B, the moving base 12 is positioned below the positioning base 11. The structure has the advantage that the accommodation space formed between the clamping arms 13A, 13B is not interfered, the clamping effect on the human tissue is improved, and the influence on the human tissue clamped between the clamping arms 13A and 13B is avoided. While it is not intended to be limited, the positioning base 11 may be disposed at a position more closer to the distal end of the actuating rod 15 depending on the actual use requirements, that is, in the illustrations shown in FIGS. 2A and 2B, the positioning base 11 is disposed at a position below the moving base 12 such that the positioning base 11 is received within the accommodation space formed between the clamping arms 13A, 13B.

In another embodiment, in the case where the moving base 12 is disposed at a position closer to the distal end of the actuating rod 15 than the positioning base 11, a first adjusting unit 151 is further provided on the actuating rod 15 at a position where the moving base is correspondingly disposed; and at the same time, a second adjusting unit 121 is provided on the moving base 12, wherein the first adjusting unit 151 and the second adjusting unit 121 are structurally adapted to provide that the moving base 12 can be rotated circumferentially and also can move axially relative to the actuating rod 15. In this embodiment, the first adjusting unit 151 is, for example, an external thread formed on the actuating rod 15, and the second adjusting unit 121 is, for example, an internal thread formed in the second penetrating channel 120 of the moving base 12. The above-described structural design has the advantage that the rotational amplitude of the clamping arms 13A, 13B can be precisely adjusted by finely controlling the amplitude of the circumferential rotation of the actuating rod 15, thereby providing a clamping force with high accuracy between the clamping arms 13A, 13B.

Figure 4A:
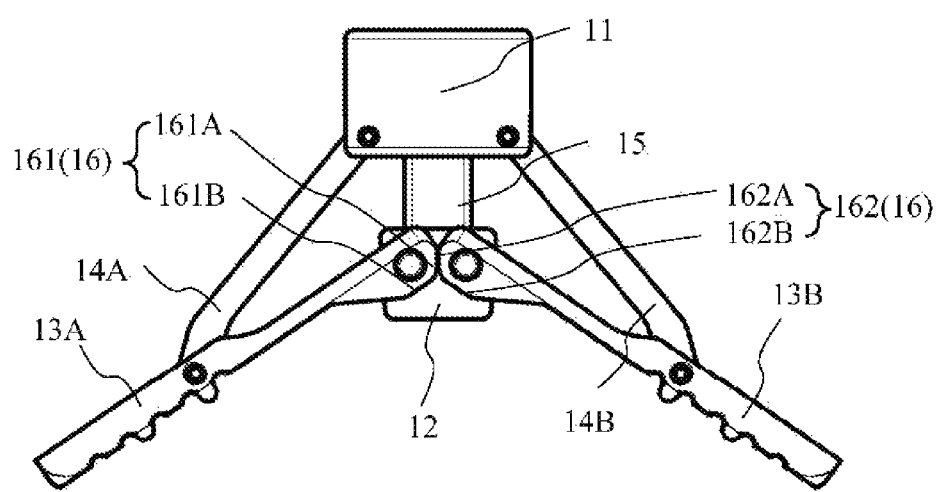
FIGS. 4A and 4B are side views of FIGS. 1A and 1B, respectively.
Figure 4B:
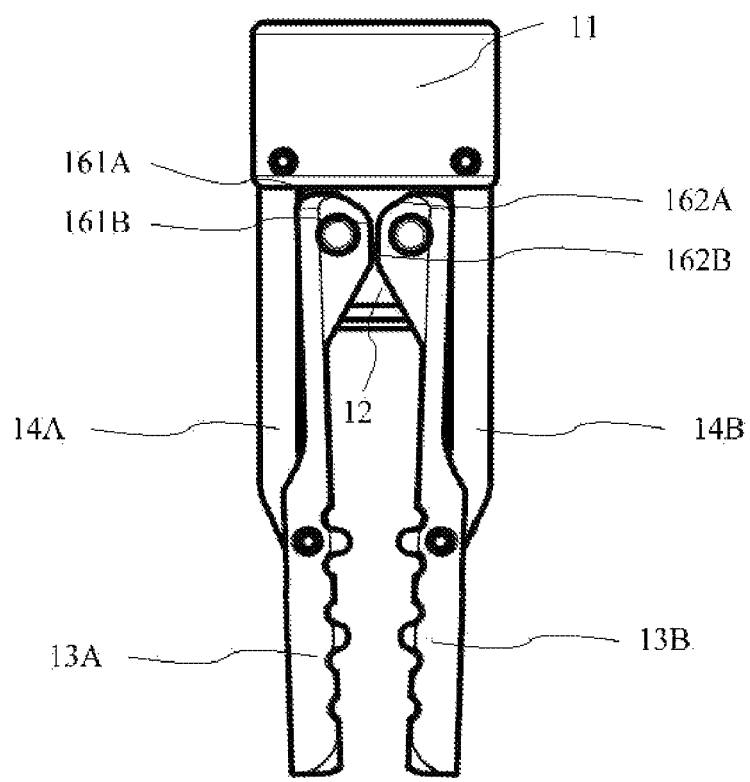

In another embodiment, the clamping instrument 1 further comprises a spacing structure 16 for defining a maximum range of movement for axial movement of the moving base 12 relative to the actuating rod 15. As shown in FIGS. 4A and 4B, in the present embodiment, the spacing structure 16 is spacing units 16A, 16B that are respectively provided at the proximal ends of the clamping arms 13A, 13B, that is, the ends of the clamping arms 13A, 13B for connecting the moving base 12. As shown in the figures, the spacing unit 16A provided at the proximal end of the clamping arm 13A has a first unfolded spacing surface 161A and a first clamping spacing surface 162A, and the spacing unit 16B provided at the proximal end of the clamping arm 13B has a second unfolded spacing surface 161B and a second clamping spacing surface 162B, wherein the first unfolded spacing surface 161A and the second unfolded spacing surface 161B coordinate to define a maximum unfolded amplitude between the clamping arms 13A and 13B (as shown in FIG. 4A), and the first clamping spacing surface 162A and the second clamping spacing surface 162B coordinate to define a minimum retraction amplitude between the clamping arms 13A and 13B (as shown in FIG. 4B). It should be noted that the design of the limiting mechanism 16 is not limited as described above and that other configurations are also suitable for use in the present application.

Figure 3:
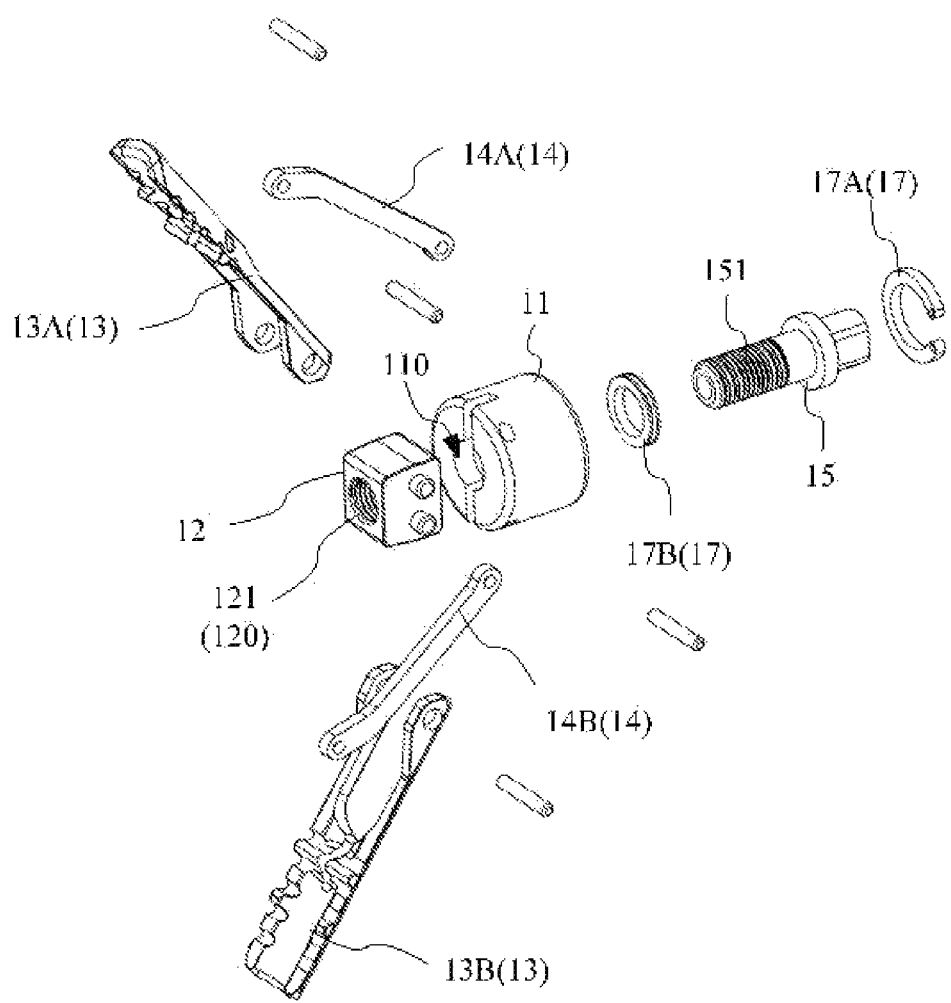
FIG. 3 is a structurally exploded view showing the clamping instrument of the first embodiment of the present application.

In addition, in another embodiment, the clamping instrument 1 further comprises a positioning structure 17 disposed between the actuating rod 15 and the positioning base 11 for limiting the axial movement of the actuating rod 15 relative to the positioning base 11 when the actuating rod 15 is rotated circumferentially. As shown in FIG. 3, in the present embodiment, the positioning mechanism 17 comprises a snap spring 17A and an anti-loosening gasket 17B which are sleeved on the actuating rod 15 and are positioned on two opposite sides of the positioning base 11, wherein the snap spring 17A is used for restricting axial movement of the positioning base 11 toward the proximal direction of the actuating rod 15 with respect to the actuating rod 15, and the anti-loosening gasket 17B is used for restricting axial movement of the positioning base 11 toward the distal direction of the actuating rod 15 with respect to the actuating rod 15. It should be noted that the design of the positioning structure 17 is not limited to the snap spring 17A and the anti-loose gasket 17B described above, but may be implemented using other elements or structural designs.

In addition, in actual operation, the clamping instrument 1 may be actuated by an external delivery device 4 to apply a force through the delivery device 4 so as to drive the clamping arms 13A and 13B of the clamping instrument 1 to perform actuation. In this embodiment, the delivery device 4 mainly comprises a delivery member 41 connected to the positioning base 11 of the clamping instrument 1 for limiting the circumferential rotation of the positioning base 11, and a driving member 42 connected to the actuating rod 15 of the clamping instrument 1 for applying an actuating force to the actuating rod 15 so as to drive the actuator rod 15 to be rotated circumferentially in a first direction (e.g., clockwise direction) or a second direction (e.g., counterclockwise direction).

Figure 7A:
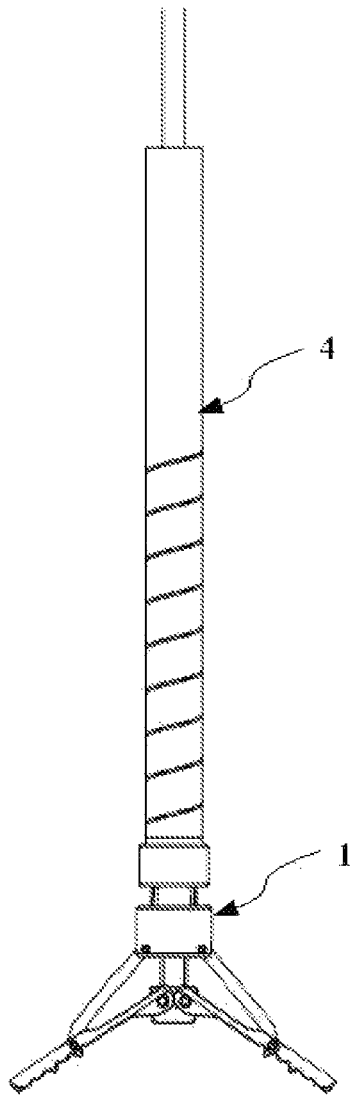
FIGS. 7A and 7B are schematic views showing an embodiment of the present application in which a clamping instrument is connected to a delivery device.
Figure 7B:
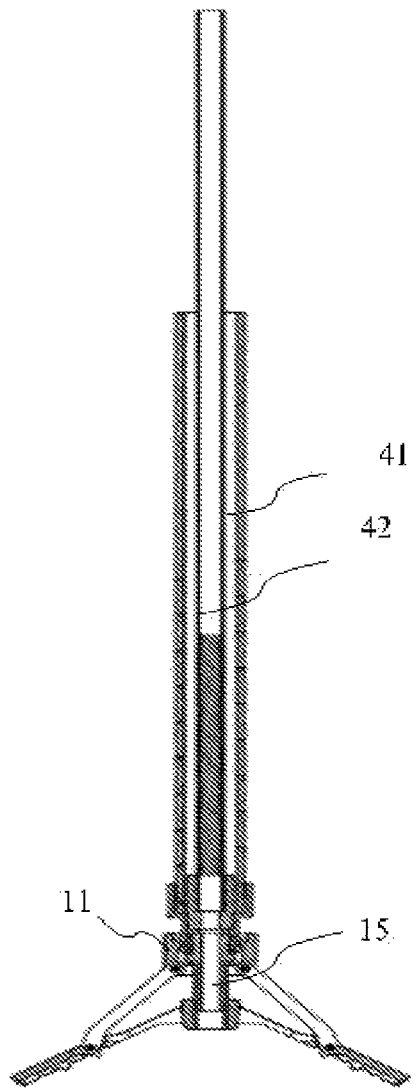
Figure 8A:
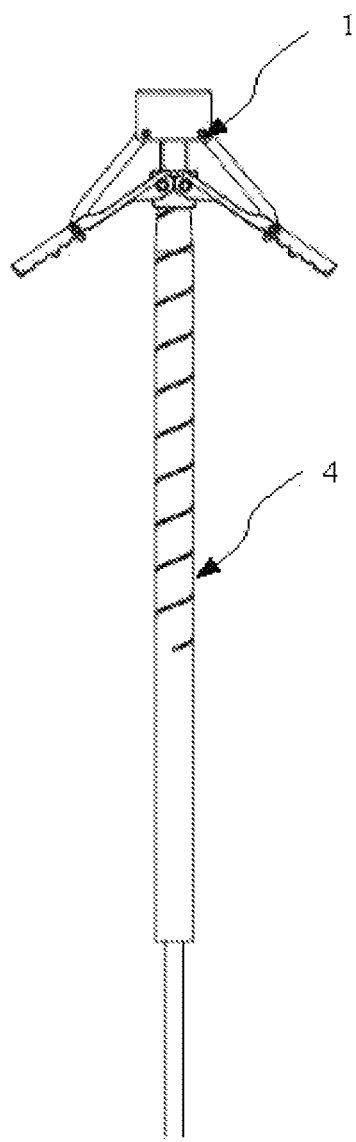
FIGS. 8A and 8B are schematic views showing another embodiment of the present application in which the clamping instrument is connected to the delivery device.
Figure 8B:
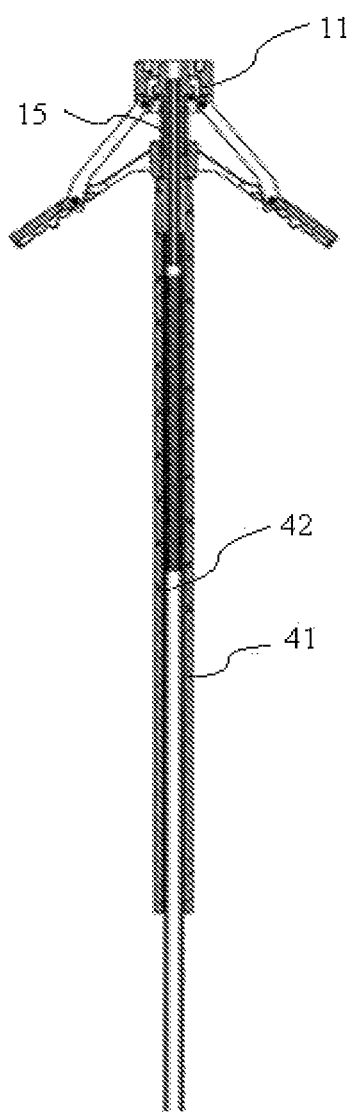
Figure 9A:
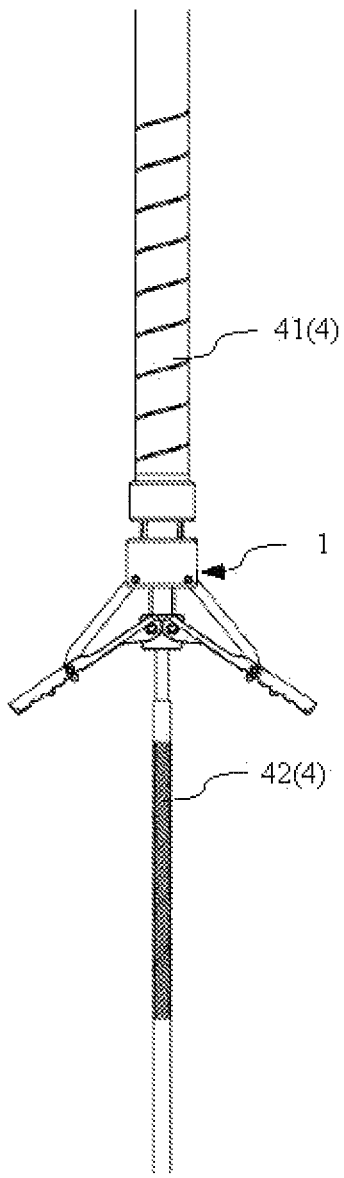
FIGS. 9A and 9B are schematic views showing yet another embodiment of the present application in which the clamping instrument is connected to the delivery device.
Figure 9B:
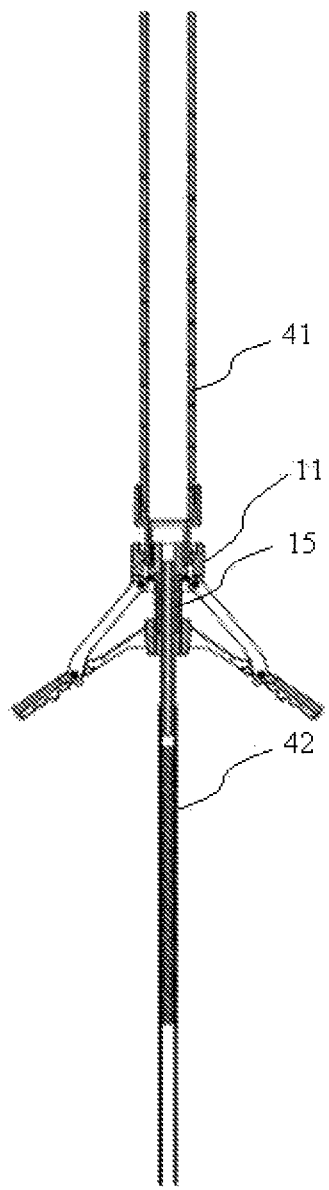

In the present application, the way of connection between the delivery device 4 and the clamping instrument 1 can be varied. For example, as shown in FIGS. 7A and 7B, in this embodiment, the delivery member 41 and the driving member 42 may be connected to the positioning base 11 and the actuating rod 15 at the proximal end of the actuating rod 15, respectively. As shown in FIGS. 8A and 8B, in another embodiment, the delivery member 41 and the driving member 42 of the delivery device 4 may also be connected to the positioning base 11 and the actuating rod 15 at the distal end of the actuating rod 15, respectively. As shown in FIGS. 9A and 9B, in yet another embodiment, the delivery member 41 and the driving member 42 of the delivery device 4 may further be connected to the positioning base 11 and the actuating rod 15 at opposite ends of the actuating rod 15, respectively. For example, the delivery member 41 is connected to the positioning base 11 at the proximal end of the actuating rod 15, and the driving member 42 is connected to the actuating rod 15 at the distal end of the actuating rod 15.

In addition, the present application also provides the clamping instrument of the second embodiment, which is mainly different from the clamping instrument 1 of the first embodiment described above in that the connection arrangement of the clamping arms and the linkage anus is exactly opposite to that of the first embodiment. That is, one end of each of the clamping arms is respectively connected to the positioning base, and two ends of each of the linkage arms are respectively connected to the moving base and each clamping arm, so that each of the clamping arms is indirectly connected with the moving base by each of the linkage arms to provide a linkage of each of the clamping anus to rotate relative to the moving base along with the change of the distance between the moving base and the positioning base. In addition, other structural design principles of the present embodiment are similar to those of the clamping instrument 1 described above in the first embodiment, and will not be described in detail herein.

Figure 5A:
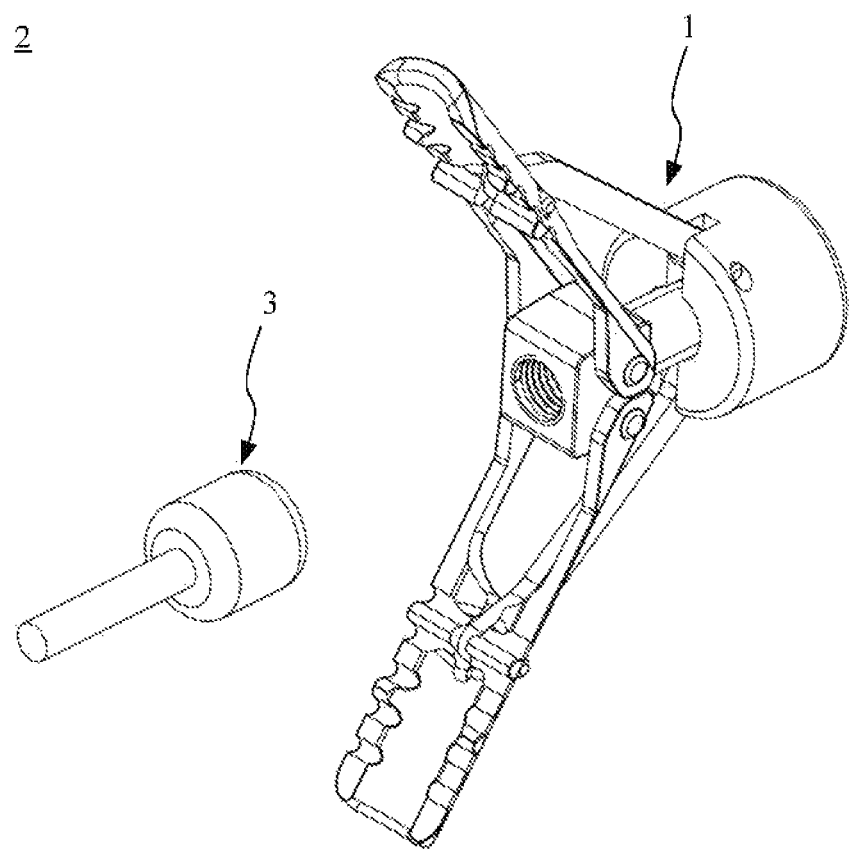
FIGS. 5A-5C are schematic views showing different embodiments of a clamping assembly of the present application.
Figure 5B:
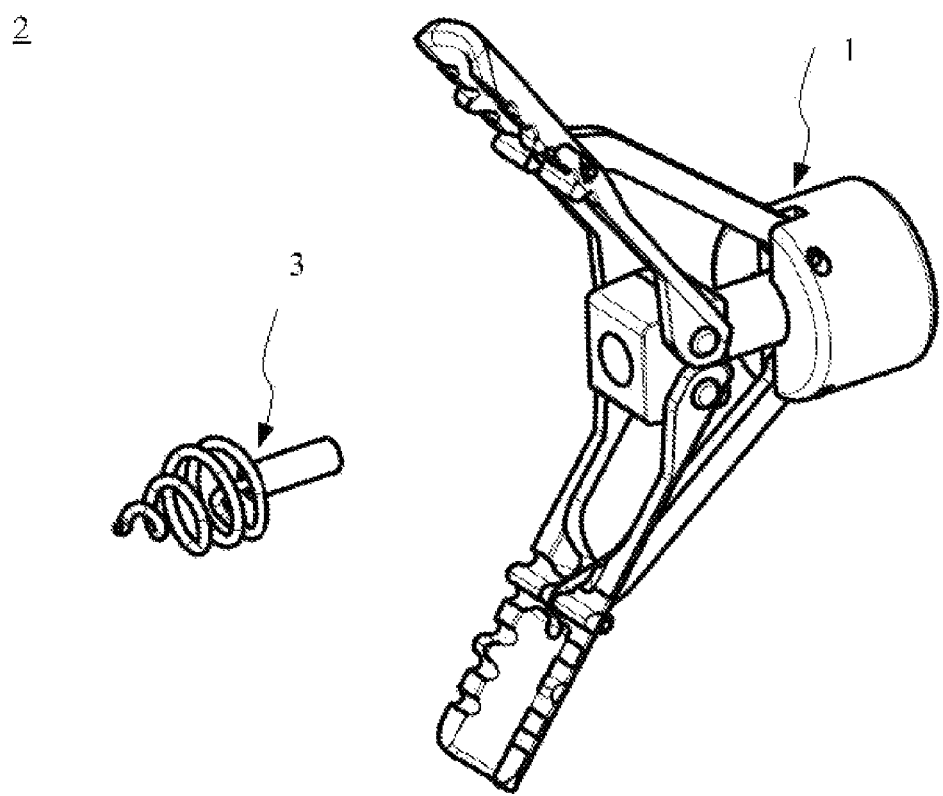
Figure 5C:
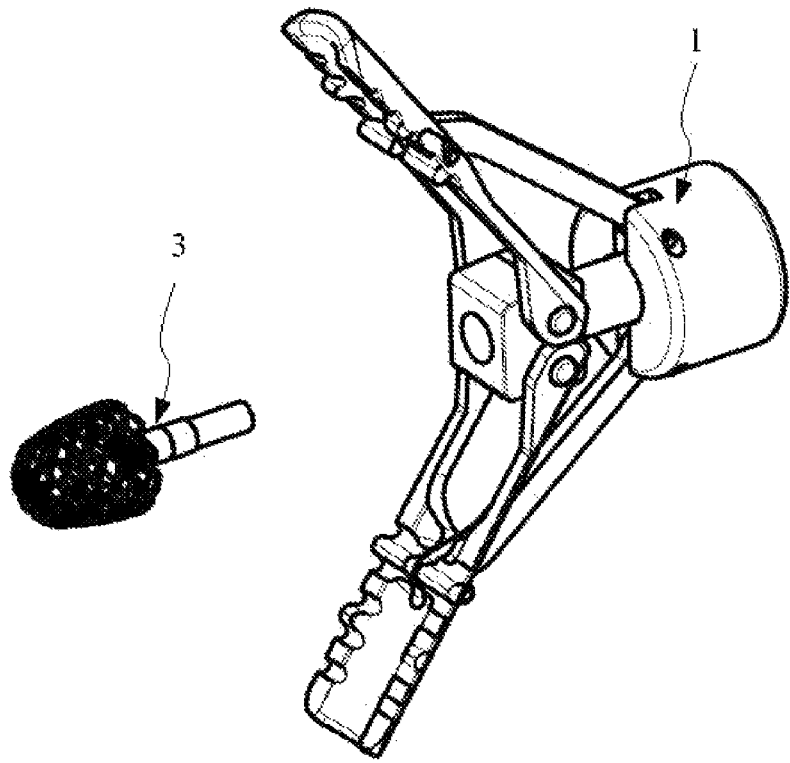

With continued reference to FIGS. 5A-5C, as well as FIGS. 6A and 6B, another embodiment of the present application also provides a clamping assembly 2 including an auxiliary support 3 and a clamping instrument 1, wherein the auxiliary support 3 is used for providing auxiliary supporting to a preset site 51 of a human tissue 5 (human valve annulus) such that the preset site 51 of the human tissue 5 is in a convex state. The clamping device 1 is used for clamping the preset site 51 in the convex state and the auxiliary support 3. In this embodiment, the main structure of the clamping instrument 1 is as described in detail in the above-mentioned embodiments, and will not be described in detail herein.

In the present embodiment, the auxiliary support 3 may be realized by various embodiments. In particular, the auxiliary support 3 may be, for example, a top bead structure (shown in FIG. 5A), a self-tapping spring wire structure (shown in FIG. 5B), or a meshed structure (shown in FIG. 5C).

With continuing reference to FIGS. 6A and 6B, in this embodiment, in an example of the auxiliary support 3 with the meshed structure, the preset site 51 of the human tissue 5 includes first and second sides 511 and 512 opposite to each other. As shown, the auxiliary support 3 is adapted to abut against the preset site 51 at the first side 511 of the preset site 51, and the clamping instrument 1 is used for clamping the preset site 51 in a convex state and the auxiliary support 3 at the second side 512 of the preset site 51, so that the preset site 51 is clamped between the auxiliary support 3 and the clamping instrument 1, thereby forming a clamping state similar to a sandwich, effectively preventing the human tissue 5 from being torn and simultaneously improving the fixing effect for the clamping.

In summary, the clamping instrument and the clamping assembly provided by the application are suitable for treating tricuspid regurgitation by a minimally invasive method, and have the advantages of being simple in structure, firm in clamping, difficult to slip and capable of preventing human tissues from being torn.

Furthermore, the actuating rod is rotated circumferentially relative to the positioning base and the moving base, so that the distance between the positioning base and the moving base is changed so as to drive the clamping arm to be rotated to clamp human tissues, achieving the technical effect of accurately controlling the rotation amplitude of the clamping arm, and providing the clamping force with high precision.

Finally, it should be noted that the above embodiments are merely illustrative of the embodiments of the present application and are not intended to be limiting thereof. Although the present application has been described in detail with reference to the foregoing embodiments, those skilled in the art will appreciate that the technical solutions of the above-mentioned embodiments can still be modified, or some of the technical features thereof can be equivalently replaced; and these modifications and substitutions do not separate the essence of the corresponding technical solutions from the spirit and scope of the embodiments of this application.

The invention claimed is:

1. A clamping instrument used for clamping a preset site of a human tissue, comprising:
a positioning base having a first penetrating channel;
a moving base having a second penetrating channel;
at least two clamping arms, wherein one end of each of the clamping arms is respectively connected with the moving base to enable each of the clamping arms to rotate around the moving base to be in an unfolded position or a clamped position;
at least two linkage arms, wherein two ends of each of the linkage arms are respectively connected with the positioning base and each of the clamping arms to enable each of the clamping arms to indirectly connect with the positioning base; and
an actuating rod, wherein the actuating rod penetrates through the first penetrating channel and the second penetrating channel respectively to enable the positioning base and the moving base to be coaxially assembled on the actuating rod, the positioning base is rotatable circumferentially around the actuating rod and is axially fixed to the actuating rod, and the moving base is rotatable circumferentially around the actuating rod and is axially movable relative to the actuating rod;
wherein, when the actuating rod is rotated circumferentially, a distance between the moving base and the positioning base can be changed, and each of the clamping arms is consequentially linked to be rotated around the moving base;
wherein, when in the unfolded position relative to the moving base, each of the clamping arms can be respectively positioned on the preset site of the human tissue; and
when each of the clamping arms is in the clamped position relative to the moving base, the preset site of the human tissue can be clamped by coordination of each of the clamping arms.

2. The clamping instrument according to claim 1, wherein when the actuating rod is rotated circumferentially in a first direction, the distance between the moving base and the positioning base is gradually reduced, so that each of the clamping arms is rotated around the moving base to be gradually rotated from the unfolded position to the clamped position; when the actuating rod is rotated circumferentially in a second direction opposite to the first direction, the distance between the moving base and the positioning base is gradually increased, so that each of the clamping arms is rotated around the moving base to be gradually rotated from the clamped position to the unfolded position.

3. The clamping instrument according to claim 2, wherein the moving base is disposed at a position closer to a distal end of the actuating rod than the positioning base.

4. The clamping instrument according to claim 1, wherein a first adjusting unit is further provided on the actuating rod at a position where the moving base is correspondingly disposed, and the moving base is provided with a second adjusting unit, wherein the first adjusting unit and the second adjusting unit are structurally adapted to enable the moving base to circumferentially rotate and axially move relative to the actuating rod, wherein the first adjusting unit is an external thread formed on the actuating rod, and the second adjusting unit is an internal thread formed in the second penetrating channel of the moving base.

5. The clamping instrument according to claim 1, wherein the clamping instrument further comprises a spacing structure for defining a maximum range of axial movement of the moving base relative to the actuating rod, the spacing structure includes two spacing units that are respectively provided at proximal ends of the two clamping arms, one of the spacing units has a first unfolded spacing surface and a first clamping spacing surface, and the other one of the spacing units has a second unfolded spacing surface and a second clamping spacing surface.

6. The clamping instrument according to claim 5, wherein the proximal ends of the two clamping arms are connected to the moving base.

7. The clamping instrument according to claim 1, wherein the clamping instrument further comprises a positioning structure disposed between the actuating rod and the positioning base for limiting axial movement of the actuating rod relative to the positioning base when the actuating rod is rotated circumferentially, the positioning structure comprises a snap spring and an anti-loosening gasket which are sleeved on the actuating rod and are positioned on two opposite sides of the positioning base.

8. The clamping instrument according to claim 1, wherein the clamping instrument is further externally connected to a delivery device, and the delivery device has:
   a delivery member having a tube with an internal diameter, the tube is connected to the positioning base of the clamping instrument for limiting the circumferential rotation of the positioning base; and
   a driving member having a rod with an external diameter, the rod is connected to the actuating rod of the clamping instrument, the external diameter is smaller than the internal diameter, so that the rod can be inserted into the tube and rotate relative to the tube to drive the actuating rod to rotate circumferentially.

9. The clamping instrument according to claim 8, wherein the delivery member and the driving member are respectively connected to the positioning base and the actuating rod at the proximal end of the actuating rod, or the delivery member and the driving member are respectively connected to the positioning base and the actuating rod at the distal end of the actuating rod, or the delivery member and the driving member are respectively connected to the positioning base and the actuating rod at two ends of the actuating rod.

10. A clamping assembly used for clamping a preset site of a human tissue, comprising:
    an auxiliary support having a bulge, the bulge provides auxiliary supporting inside the human tissue to enable the preset site of the human tissue to be in a convex state; and
    a clamping instrument according to claim 1 for clamping the preset site in the convex state and the auxiliary support.

11. The clamping assembly according to claim 10, wherein the preset site comprises a first side and a second side opposite to each other, wherein the auxiliary support is configured to abut against the preset site at the first side of the preset site, and the clamping instrument is configured to clamp the preset site and the auxiliary support at the second side of the preset site, so that the preset site is clamped between the auxiliary support and the clamping instrument.

12. A clamping instrument used for clamping a preset site of a human tissue, comprising:
    a positioning base having a first penetrating channel;
    a moving base having a second penetrating channel;
    at least two clamping arms, wherein one end of each of the clamping arms is respectively connected with the positioning base to enable each of the clamping arms to rotate around the positioning base to be in an unfolded position or a clamped position;
    at least two linkage arms, wherein two ends of each of the linkage arms are respectively connected with the moving base and each of the clamping arms to enable the clamping arms to indirectly connect with the moving base; and
    an actuating rod, wherein the actuating rod penetrates through the first penetrating channel and the second penetrating channel respectively to enable the positioning base and the moving base to be coaxially assembled on the actuating rod, the positioning base is rotatable circumferentially around the actuating rod and is axially fixed to the actuating rod, and the moving base is rotatable circumferentially around the actuating rod and is axially movable relative to the actuating rod;
    wherein, when the actuating rod is rotated circumferentially, a distance between the moving base and the positioning base can be changed, and then each of the clamping arms is consequentially linked to be rotated around the moving base;
    wherein, when in the unfolded position relative to the moving base, each of the clamping arms can be respectively positioned on the preset site of the human tissue; and
    when each of the clamping arms is in the clamped position relative to the moving base, the preset site of the human tissue can be clamped by coordination of each of the clamping arms.

13. The clamping instrument according to claim 12, wherein the positioning base is disposed at a position closer to a distal end of the actuating rod than the moving base.

14. The clamping instrument according to 12, wherein the clamping instrument is further externally connected to a delivery device, and the delivery device has:
    a delivery member having a tube with an internal diameter, the tube is connected to the moving base of the clamping instrument for limiting the circumferential rotation of the moving base; and
    a driving member having a rod with an external diameter, the rod is connected to the actuating rod of the clamping instrument, the external diameter is smaller than the internal diameter, so that the rod can be inserted into the tube and rotate relative to the tube to drive the actuating rod to rotate circumferentially.

\* \* \* \* \*